United States Patent [19]

Arp

[11] Patent Number: 5,165,397
[45] Date of Patent: Nov. 24, 1992

[54] METHOD AND APPARATUS FOR DEMAND OXYGEN SYSTEM MONITORING AND CONTROL

[76] Inventor: Leon J. Arp, 1107 Highland Cir., Blacksburg, Va. 24060

[21] Appl. No.: 561,367

[22] Filed: Jul. 31, 1990

Related U.S. Application Data

[63] Continuation of Ser. No. 285,861, Dec. 15, 1988, abandoned.

[51] Int. Cl.⁵ ............................................. A61M 16/00
[52] U.S. Cl. .......................... 128/204.21; 128/204.23; 128/205.23; 128/204.26
[58] Field of Search .................... 128/204.18-204.26, 128/716, 722, 723; 364/413.03, 413.05

[56] References Cited

U.S. PATENT DOCUMENTS

| | | | |
|---|---|---|---|
| 2,912,979 | 11/1959 | Lieber | 128/204.26 |
| 3,191,595 | 6/1965 | Wilson | 128/204.26 |
| 3,267,935 | 8/1966 | Andreasen et al. | 128/204.18 |
| 3,400,713 | 9/1968 | Finan | 128/204.18 |
| 3,493,703 | 2/1970 | Finan | 128/204.26 |
| 3,566,387 | 2/1971 | Schoener et al. | 128/204.18 |
| 3,794,059 | 2/1974 | Burt | 128/204.22 |
| 3,831,596 | 8/1974 | Cavallo | 128/204.26 |
| 4,050,458 | 9/1977 | Friend | 128/204.23 |
| 4,054,133 | 10/1977 | Myers | 128/204.18 |
| 4,278,110 | 7/1981 | Price et al. | 128/204.24 |
| 4,323,064 | 4/1982 | Hoenig | 128/204.21 |
| 4,336,590 | 6/1982 | Jacq et al. | 128/204.18 |
| 4,381,002 | 4/1983 | Mon | 128/204.18 |
| 4,414,982 | 11/1983 | Durkan | 128/204.24 |
| 4,457,303 | 7/1984 | Durkan | 128/204.24 |
| 4,459,982 | 7/1984 | Fry | 128/204.23 |
| 4,461,293 | 7/1984 | Chen | 128/204.23 |
| 4,462,398 | 7/1984 | Durkan et al. | 128/204.24 |
| 4,484,578 | 11/1984 | Durkan | 128/204.24 |
| 4,506,666 | 3/1985 | Durkan | 128/204.24 |
| 4,519,387 | 5/1985 | Durkan et al. | 128/204.24 |
| 4,535,766 | 8/1985 | Baum | 128/204.23 |
| 4,537,190 | 8/1985 | Caillot | 128/204.23 |
| 4,565,194 | 1/1986 | Weerda et al. | 128/204.23 |
| 4,567,888 | 2/1986 | Robert et al. | 128/204.21 |
| 4,570,631 | 2/1986 | Durkan | 128/204.23 |
| 4,579,115 | 4/1986 | Wallroth | 128/204.21 |
| 4,587,967 | 5/1986 | Chu | 128/204.21 |
| 4,612,928 | 9/1986 | Tiep | 128/204.23 |
| 4,648,396 | 3/1987 | Raemer | 128/204.22 |
| 4,744,356 | 5/1988 | Greenwood | 128/204.26 |
| 4,784,130 | 11/1988 | Kenyon | 128/204.26 |
| 4,823,788 | 4/1989 | Smith | 128/204.18 |
| 4,883,050 | 11/1989 | Urman | 128/204.23 |
| 4,915,103 | 4/1990 | Visveshwara | 128/204.23 |
| 5,003,985 | 4/1991 | White | 128/716 |

*Primary Examiner*—David A. Wiecking
*Assistant Examiner*—Steven S. Kelley
*Attorney, Agent, or Firm*—Rockey, Rifkin and Ryther

[57] ABSTRACT

An apparatus and method for controlling a respirating gas supply system responsive to a patient's respiration. The ratio of the time of the gas supply valve open to the time of the valve closed is measured and an automatic oxygen flow override is provided if the ratio is outside a set range. Various indicators quickly indicate to the operator what system or systems have failed and/or the condition of the patient's respiration. The apparatus can operate in two modes: a pre-flush mode which would begin gas flow to the patient at the end of exhalation and end gas flow at the end of inhalation and an inhalation mode which would begin gas flow at the beginning of inhalation and end gas flow at the end of inhalation.

9 Claims, 4 Drawing Sheets

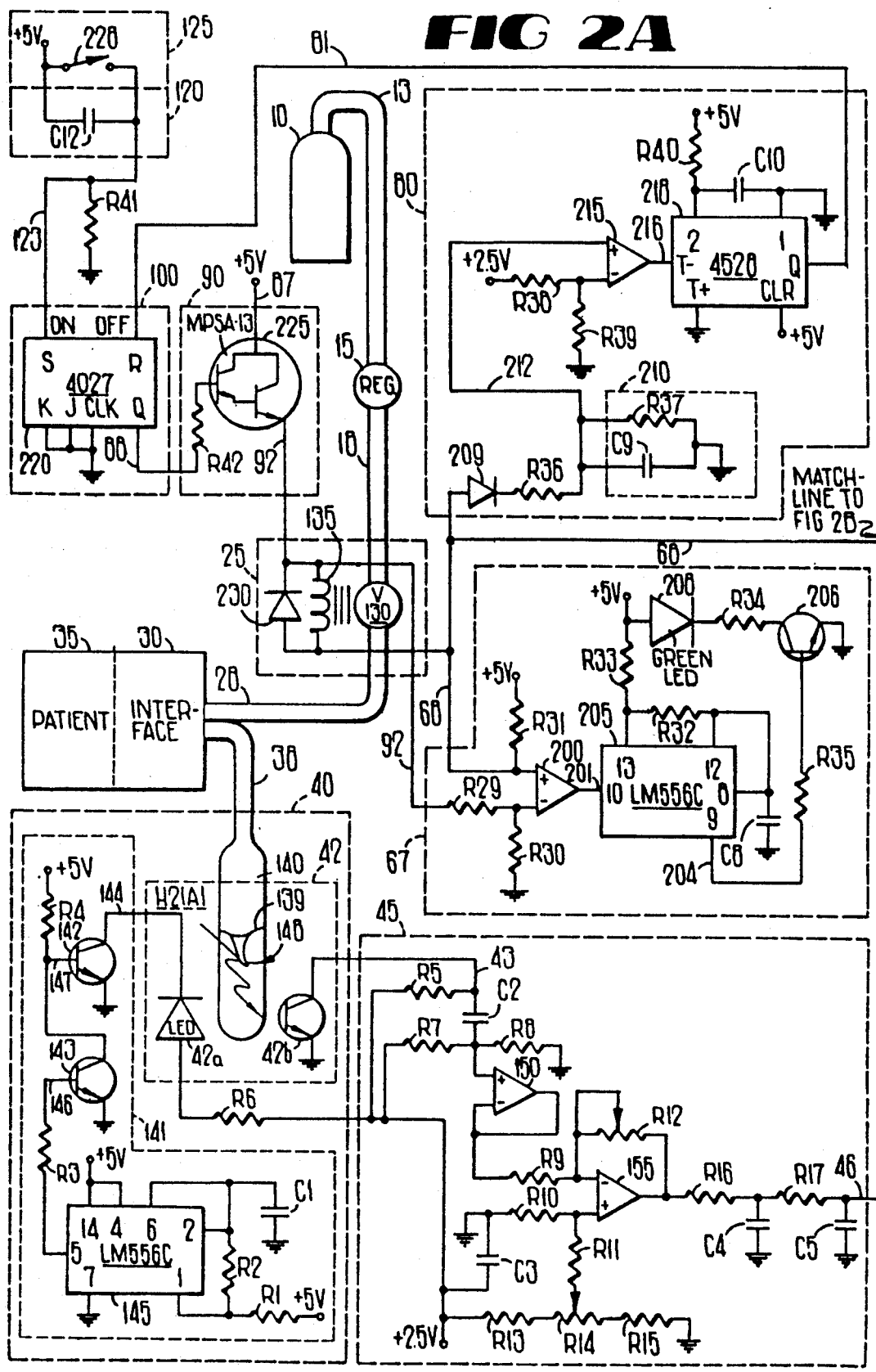

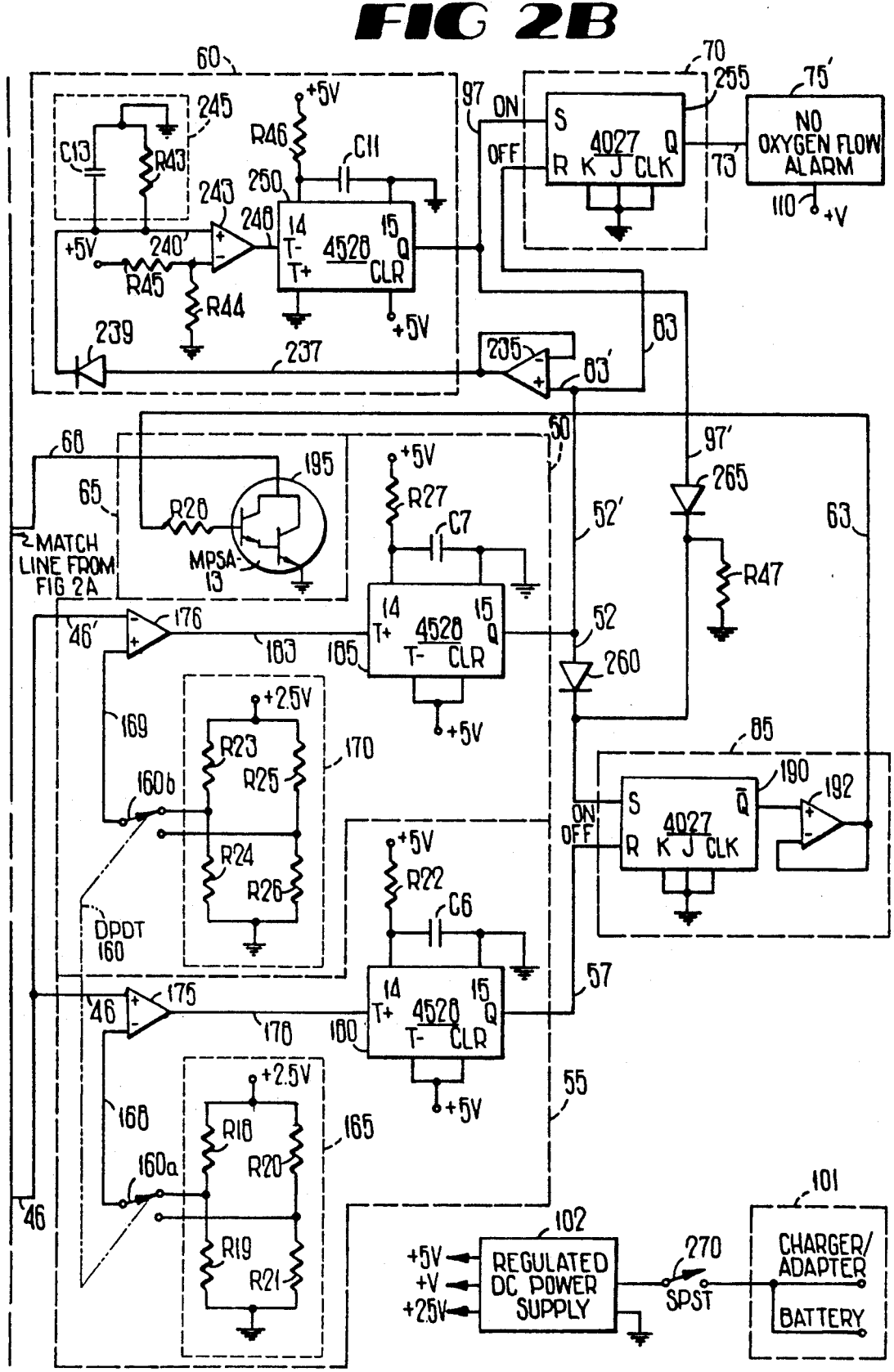

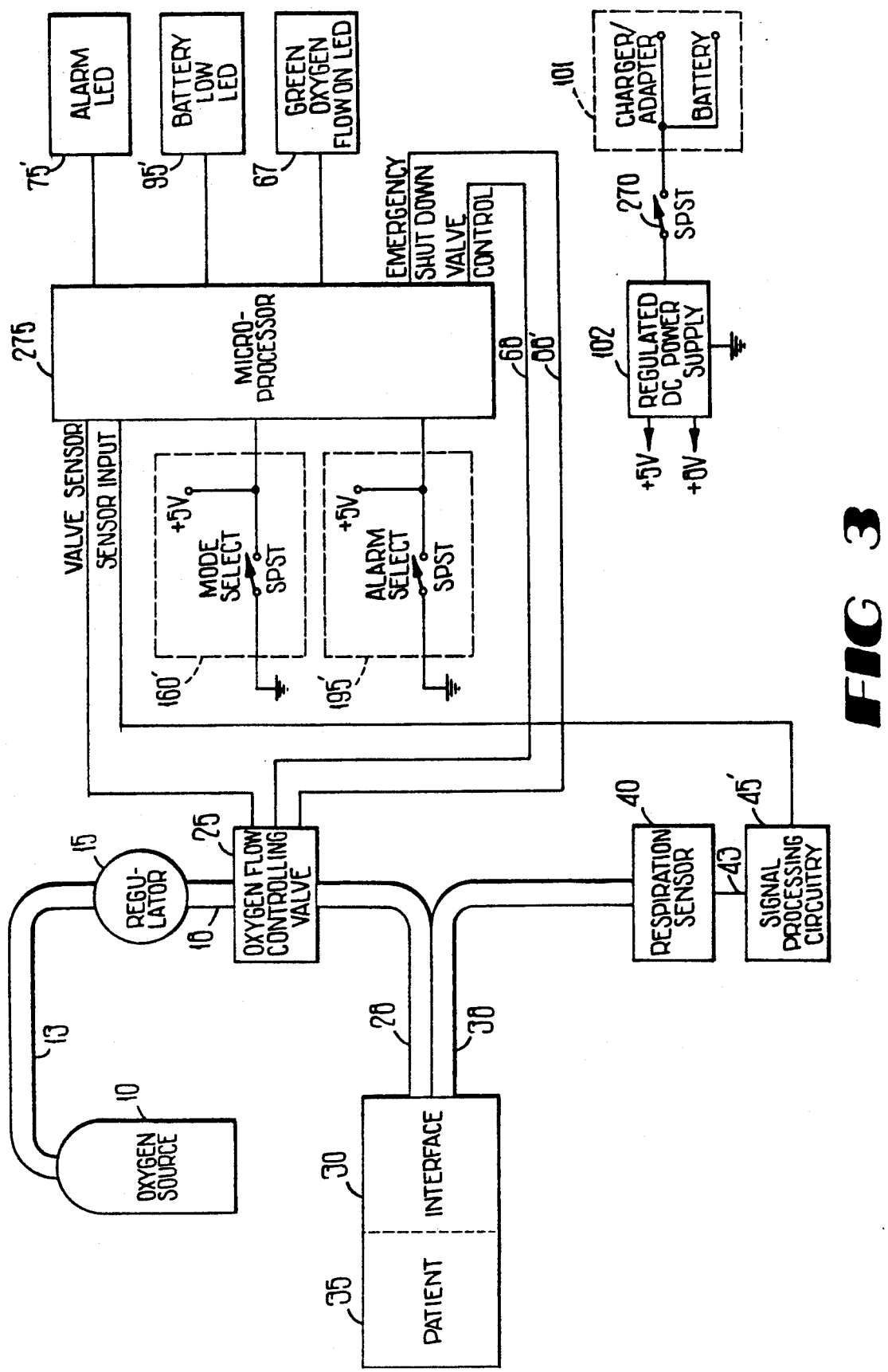

METHOD AND APPARATUS FOR DEMAND OXYGEN SYSTEM MONITORING AND CONTROL

This is a continuation of U.S. Ser. No. 285,861 filed Dec. 15, 1988 now abandoned.

TECHNICAL FIELD

The present invention relates generally to the art of flow monitoring and fluid flow control and particularly provides an improved demand oxygen apparatus for providing supplemental oxygen to a patient and means for the detection and notification of various operational states of a demand oxygen system.

BACKGROUND OF THE INVENTION

Many patients with lung or breathing disorders require oxygen enrichment of the air they breathe. This supplemental oxygen is delivered at a constant flow rate to the patient through nasal tubes called cannulae or through face masks. Cannulae are two short pieces of plastic tubing attached to one end of a plastic hose. The two short pieces of plastic tubing fit into the nasal passages. The other end of the plastic hose is attached to the oxygen source. A face mask is a mask which fits over the mouth and nose and is attached to one end of a plastic hose. The other end of the plastic hose is attached to the oxygen source. The most common practice for enriching the concentration of oxygen in the gas inhaled by a patient is to connect the oxygen delivery tubing to a flow meter which is, in turn, connected to the oxygen source. The flow meter allows the flow rate of oxygen, in liters per minute, to be read from a scale on the flow meter and provides a means for selecting and varying the flow rate of oxygen which is delivered to the patient. This most commonly used method of administering supplemental oxygen to a patient provides a constant flow of oxygen and does not provide for monitoring of the patient's breathing cycle, of the presence or absence of oxygen flow, or for automatic control of the flow of oxygen to the patient.

One type of system to supply oxygen to a patient is a demand oxygen system. Cost containment and reduction of the cost of medical care continues to be a major concern both to the federal and state agencies that pay much of the cost of medical treatment and to the public at large who eventually pay all the costs of treatment through taxes, insurance premiums, and direct billings. Although oxygen is only a small part of total medical costs, it is a large and economically significant aspect of in-hospital and at-home medical treatment costs. A demand oxygen system is an oxygen control apparatus which provides oxygen upon demand and not continuously. By providing oxygen on demand, a savings is realized by the hospital and/or patient using the oxygen.

Patient respiration occurs in two phases: inhalation and exhalation. Patients receiving oxygen therapy utilize the oxygen delivered only during the inhalation phase of respiration. No oxygen flow is required by the patients during exhalation. The current practice, however, is to allow the oxygen to flow continuously to the patient. The cost efficiency of providing oxygen only during inhalation is known to those skilled in the art. Methods have been devised to detect respiration and differentiate between inhalation and exhalation. U.S. Pat. No. 4,567,888, issued to Robert et al., on Feb. 4, 1986 describes one such method using a thermistor-triggered electrical valve control to control the oxygen supply during oxygen therapy. The temperature sensing thermistor described in Robert et al. is placed in close contact with the air inhaled and exhaled from the patient. The higher temperature of the air exhaled indicates when exhalation is taking place. The temperature drop sensed when inhalation takes place cues the controller to provide oxygen during the inhalation part of the breathing cycle. In this way, the Robert et al. apparatus is a "demand oxygen system" because it is the function of inhalation which demands the oxygen to be provided to the patient.

Demand oxygen systems are most commonly used in hospitals for patients who require supplemental oxygen to breathe. There are also portable demand oxygen systems for persons with chronic lung ailments. Numerous systems have been devised for monitoring and controlling the flow of oxygen in demand oxygen systems. The quality of the demand oxygen system is directly proportional to the monitoring capabilities of the system. If the person attending a patient is unable to determine the operational status of the demand oxygen system, the demand oxygen system is not doing its job. One drawback of prior art demand oxygen systems is the size required for the systems. In a hospital setting, a large demand oxygen system presents minimal difficulties. In a portable unit, though, it is necessary for the oxygen flow controller to be small.

A patient using a demand oxygen system is able to breathe on his own. In fact, it is the patient's breathing which triggers the operation of the demand oxygen system. When a patient has trouble breathing, a good demand oxygen system should be able to detect such trouble. It is old in the art to detect an irregularity in a patient's breathing. U.S. Pat. No. 4,461,293 issued to Chen describes an apnea event detection device which detects when the patient's breathing has stopped and reacts to dislodge an obstruction from the breathing canal. Most of the prior art devices use a clock and an operator set time after inhalation to look for the next inhalation. If inhalation does not occur within the time permitted, an apnea event is detected. This method of detecting trouble with a patient's breathing has drawbacks. The operator sets the time which determines apnea event detection. This time could vary from patient to patient and also vary depending upon the patient's state: i.e., if the patient is awake or asleep.

It is known in the art to continuously provide oxygen upon the detection of an irregularity in the patient's breathing. When a failure occurs in the control system, though, the prior devices do not provide a continuous flow of oxygen. For example, if the respiration sensor fails, the patient's breathing could not be properly monitored and the demand oxygen system would not properly function. Another hazard in a demand oxygen system is that, since the oxygen flow is controlled by a valve which opens and closes, there is the possibility that the system would malfunction with the valve in the closed position. It is unsatisfactory for the patient to have to advise the operator that he is not receiving any oxygen.

SUMMARY OF THE INVENTION

The present invention overcomes the deficiencies in the prior art by providing sufficient backup oxygen delivery indicators for the patient and/or operator to be aware of the operation of the machine, and a safer and more efficient oxygen delivery to the patient by constant monitoring of the patient's respiration. The present system consists of a selectable means for selecting an ON or OFF condition for visible and audible alarms. When the alarms are OFF, an indicator on the front panel indicates such alarm OFF condition. When the alarms are turned ON, they will light up and sound when the input voltage falls below a level sufficient to operate the demand oxygen system or when there is no oxygen flow. No oxygen flow could occur from a blockage in the cannulae providing oxygen flow to the patient or from an empty oxygen cannister. Other features of the invention are a green and red indicator to show when the oxygen flow controlling valve is open and when it is closed, respectively. A visible indicator shows whether the patient's inhalation has fallen below a level which is variably set. If the ratio of the time of exhalation to the time of inhalation exceeds the operably set ratio, an indicator is lighted up on the control panel and oxygen is continuously provided to the patient.

Another improvement allows oxygen to be supplied from the end of exhalation to the beginning of exhalation. When oxygen is only supplied after the beginning of inhalation, the first gas mixture inhaled out of a face mask or from a nasal cannula is a volume of carbon dioxide from the preceding exhalation which remained in the face mask or nasal airway. If oxygen flow is started at the end of exhalation, the flow of oxygen washes out and dilutes the carbon dioxide which remained in the face mask or nasal airway from the preceding exhalation. This wash-out and dilution of carbon dioxide occurs because normally there is a short period of time which elapses between the end of exhalation and the beginning of inhalation. The oxygen flow, when started at the end of exhalation, washes out and dilutes the carbon dioxide from the previous exhalation. In this manner, not only is oxygen conserved, but the patient breathes in more oxygen and less carbon dioxide.

The valve in the preferred embodiment of the invention which controls the oxygen flow is a normally open valve. Therefore, when no power is applied to the valve, it remains in the open position. The preferred invention provides a power interruption switch which interrupts the power provided to the oxygen flow controlling valve when certain failure conditions occur. For example, if the circuit which controls the opening and closing of the valve fails in the valve closed mode, the power interruption switch will activate and open the valve. Also, if it is determined that there is insufficient power to open and close the valve due to a malfunction in the power supply, the power interruption switch will open the valve for continuous oxygen flow. Also, if the respiration sensor in the preferred embodiment of the machine malfunctions, the device is unable to measure the inhalation and exhalation ratios of the patient. Being unable to measure the inhalation and exhalation ratios, the device will provide a continuous flow of oxygen to the patient.

Therefore, generally stated, it is the object of the present invention to overcome the drawbacks in prior art demand oxygen systems recited above.

More specifically, it is an object of the present invention to provide oxygen flow to a patient during the inhalation phase of respiration, turning off the oxygen flow at the end of inhalation.

It is further object of the present invention to provide improved oxygen provision by providing oxygen to the patient at the end of exhalation, turning off the oxygen flow at the beginning of exhalation. In this manner, the first breath breathed in by the patient contains a much smaller concentration of carbon dioxide and a much larger concentration of oxygen.

It is a further object of the present invention for the patient and/or the attending personnel to be able to determine at what point in the respiration cycle that the oxygen flow is to be turned on. The patient and/or the attending personnel can also determine the point in the respiration cycle at which the oxygen flow will be turned off.

It is a further object of the present invention that if the device fails or the valve is not turned on to provide oxygen, a continuous flow of oxygen is provided to the patient.

It is a further object of the present invention to provide visible and audible signals to the patient and/or the attending personnel if the source of oxygen is not turned on or the source of oxygen is depleted.

It is a further object of the present invention to provide visible and audible signals to the patient and/or the attending personnel if the patient's respiration is insufficient to trigger proper oxygen flow within a preselected ratio of time of oxygen valve open to time of oxygen valve closed ratio. A weak exhalation or inhalation by the patient would cause the visible and audible signals to activate. Also, if the ratio of the patient's inhalation to exhalation is outside permissible limits, the visible and audible signals would activate and oxygen flow to the patient would be started automatically.

It is a further object of the present invention that a continuous flow of oxygen be provided to the patient when the patient's respiration falls outside a preselected inhalation to exhalation ratio.

It is still a further object of the present invention to provide a demand oxygen system which is economical for hospitals and individual users.

It is a further object of the present invention to provide a demand oxygen system which is durable, efficient, and reliable and which is economical to manufacture.

It is a further object of the present invention to provide a demand oxygen system which is compact enough for use with a portable oxygen delivery system.

It is still a further object of the present invention to provide a demand oxygen system which is less likely to fail due to the fact that it has relative few components in the controller.

That the present invention satisfies these objects, and overcomes the drawbacks of the prior art, will be appreciated from the detailed description of the preferred embodiment below.

BRIEF DESCRIPTION OF THE DRAWINGS

FIG. 2, consisting of FIGS. 2A and 2B, is a schematic diagram of a first embodiment of the invention.

FIG. 3 is a diagram of the preferred embodiment of the invention.

DETAILED DESCRIPTION

Figure 1:
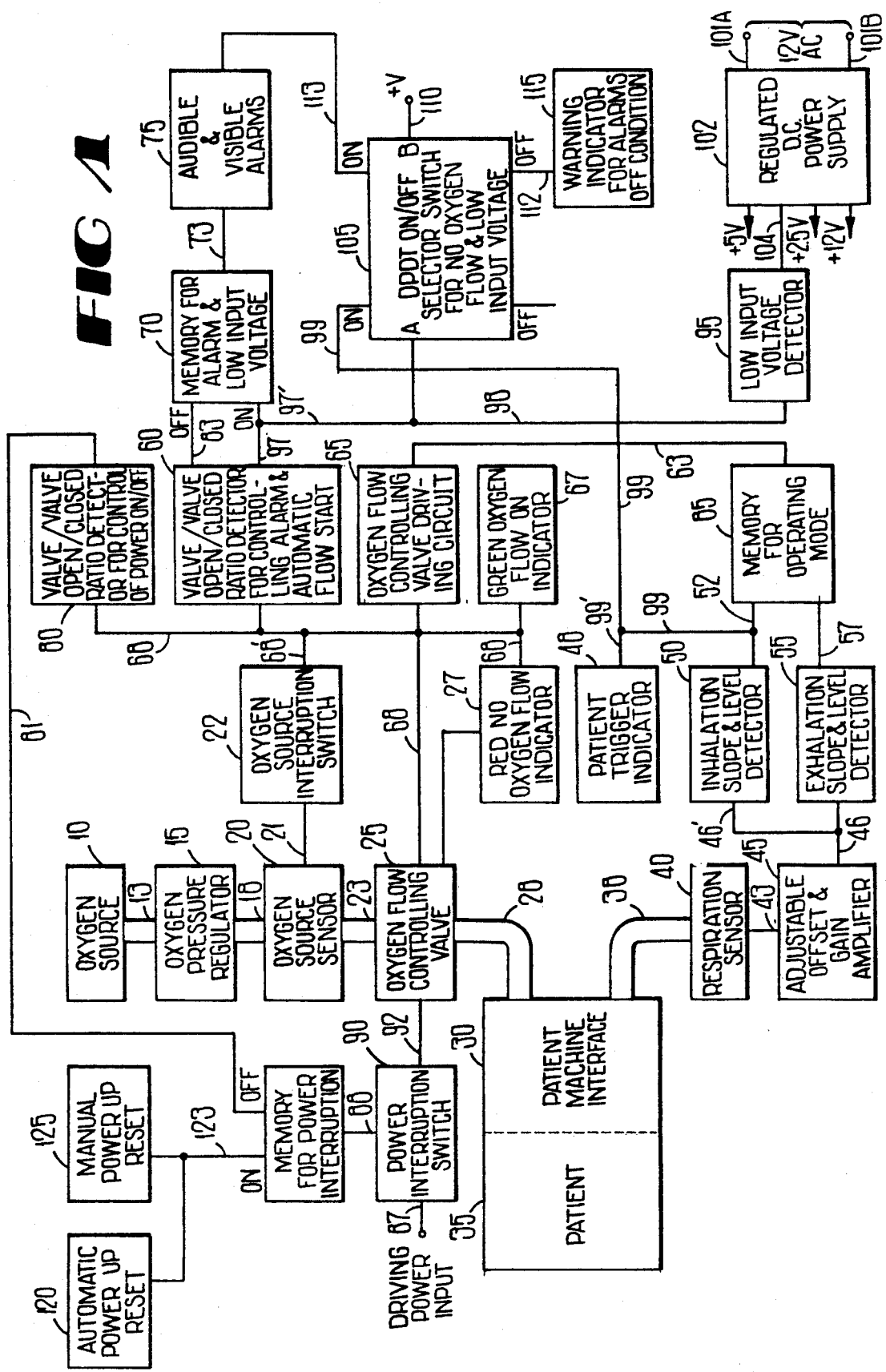
FIG. 1 is a block diagram of the invention.

Turning next to the drawings in which like numerals represent like parts, the preferred embodiment of the present invention will now be described. FIG. 1 is a block diagram showing the electrical and mechanical parts of the preferred embodiment. An oxygen source 10 is connected by fluid path 13 to fluid pressure regulator 15. In hospital use, fluid source 10 could be a central location for oxygen or some other gas mixtures containing oxygen. In the case of a mobile patient needing oxygen, fluid source 10 can be a canister of oxygen.

Pressure regulator 15 is of a kind well known to those skilled in the art. It controls the fluid flow so that a steady pressure of fluid is placed in fluid path 18. The fluid passes through source sensor 20 and thence to the oxygen flow controlling valve 25 by fluid path 23. Oxygen source sensor 20 is a device which senses whether oxygen is present in fluid path 18. If no oxygen is present in fluid path 18, oxygen source sensor 20 causes oxygen source interruption switch 22 to close. Source sensor 20 is connected to oxygen source interruption switch 22 by a mechanical-to-electrical connection 21. The closing of oxygen source interruption switch 22, explained in detail below, causes red no oxygen flow indicator 27 to light up continuously and activates the audible and visible alarms 75, thereby informing the operator that no oxygen is flowing from oxygen pressure regulator 15.

Oxygen flow controlling valve 25 is an electrical-to-mechanical device which controls the flow of oxygen to the patient 35. Valve 25 in the preferred embodiment is a normally open valve. This means that when no voltage is applied to the electrical controls of valve 25, the valve is open and allows oxygen to flow through valve 25 into fluid path 28. It can be understood by those skilled in the art that a normally closed valve would also work for valve 25. Electrical controls for valve 25 are such that in the default mode when it is determined that a patient is having trouble breathing, valve 25 is in the open position. When valve 25 is open, oxygen is provided via fluid path 28 to patient-machine interface 30. The electrical and mechanical portions of valve 25 are of construction well known to those skilled in the art.

Patient-machine interface 30 can be any of numerous types of oxygen providing methods. For example, interface 30 could be a face mask, which fits over the nose and mouth, into which patient 35 breathes. Interface 30 could also be a tracheal tube which is inserted into the patient's trachea for in vivo oxygen supply. Also, interface 30 could be a nasal cannulae with tubes which fit in the nasal passages of patient 35.

Connected to patient-machine interface 30 via path 38 is respiration sensor 40. Respiration sensor 40 measures inhalation and exhalation of patient 35 through the use of an optodetector pair 42, consisting of a light emitting diode and a phototransistor (FIG. 2), or may be a conventional, commercially available pressure of flow detector.

The signal from respiration sensor 40 indicating whether patient 35 is inhaling or exhaling is carried to adjustable offset and gain amplifier 45 via line 43. The signal is then carried to exhalation slope and level detector 55 and inhalation slope and level detector 50 via lines 46 and 46', respectively. Whether the slope of the signal is positive or negative determines whether it is indicative of inhalation or exhalation. Inhalation slope and level detector 50 will act upon a positive going signal, while exhalation slope and level detector 55 will act upon a negative going signal provided from respiration sensor 40 via adjustable and offset gain amplifier 45. Slope and level detectors 50 and 55 serve to operate valve 25 via signals to valve driving circuitry 65 on line 63. Oxygen flow controlling valve driving circuit 65 receives input from memory for operating mode 85 via line 63. The signals leaving detectors 50 and 55 on lines 52 and 57, respectively, are processed by memory for operating mode 85 to determine the signal to provide to driving circuitry 65 in line 63.

Each time patient 35 causes inhalation slope and level detector 50 to produce a signal to start oxygen flow to patient 35, the same signal causes patient trigger indicator 48 to light up via line 99'. Valve open/valve closed ratio detector for controlling alarm and automatic oxygen flow 60 detects the ratio of the time in which oxygen flow controlling valve 25 is open as compared to the time in which oxygen flow controlling valve 25 is closed. If the ratio detected is outside of an operator adjustable acceptable range, detector 60 triggers audible and visible alarm 75 by placing memory for alarm and low input voltage 70 into the ON condition. This is done by placing a signal upon line 97 which is connected to the ON of memory 70. The signal on line 97 is also provided via line 97' and 99 to the inhalation input (line 52) of memory for operating mode 85. In other words, a signal on line 99 from ratio detector 60 holds memory for operating mode 85 in an inhalation condition which means driving circuitry 65 will keep valve 25 in an open position. Thus, until ratio detector 60 detects an operator acceptable ratio of inhalation to exhalation, a continuous flow of oxygen will be provided to the patient. When ratio detector 60 detects an operator acceptable ratio of inhalation rate to exhalation rate, detector 60 places a signal on line 83 to the OFF input of memory 70, thereby deactivating audible and visible alarms 75.

Oxygen flow controlling valve 25 is open and closed by signals from oxygen flow controlling valve driving circuit 65 provided on line 68. The valve driving signal on 68 is also provided to ratio detector 60 and valve open/valve closed ratio detector for control of power on/off 80 so that detectors 60 and 80 can calculate the ratios. If the ratios are within the operator set acceptable ranges detectors 60 and 80 will not output a signal on lines 97 and 81, respectively. The operator can set the values at which ratio detectors 60 and 80 should register a signal of the ratio of valve open to valve closed time unacceptable. This allows the oxygen monitoring system to be reset for each different patient and reset for each different breathing mode of the patient. The valve control signal on line 68 is also connected to red no oxygen flow indicator 27 and green oxygen flow on indicator 67. When the valve control signal on line 68 is high, valve 25 is activated, thereby closing valve 25 and red no oxygen flow indicator 27 is lit. When the valve control signal on line 68 goes low, oxygen flow controlling valve 25 is deactivated, thereby opening valve 25, allowing oxygen to flow to the patient. This also causes green oxygen flow on indicator 67 to be lit. Oxygen source interruption switch 22 is connected to line 68 via line 68'. If oxygen source sensor 20 detects no oxygen, oxygen source interruption switch 22 produces a control signal on line 68 which will in turn set off audible and visible alarm 75. The control signal on line 68 also lights up red no oxygen flow indicator 27.

The control signal on line 68 is provided to oxygen flow controlling valve 25. Valve driving power 87 is provided to oxygen flow controlling valve 25 via power interruption switch 90 and line 92. Power interruption switch 90 is provided between the valve driving power input 87 and valve 25 so that if a failure condition occurs, the power to valve 25 is interrupted by switch 90 so that valve 25 goes into the default mode, being instantly open. Valve open/valve closed ratio detector 60 will always have a smaller absolute value to cause its output to produce a signal to line 97 than what is required for valve open/valve closed ratio detector 80 to produce a signal to line 81. Therefore, if valve open/valve closed ratio detector 80 ever produces a signal to line 81, the output from valve open/valve closed ratio detector 60 would always have produced a signal to activate audible and visible alarms 75 just prior to the output signal from valve open/valve closed ratio detector 80. An output signal to line 81 from valve open/valve closed ratio detector 80 would cause the memory for power interruption circuit 100 to deliver a signal on line 88 to activate the power interruption switch 90. Activation of the power interruption switch 90 would place valve 25 in an open position providing continuous oxygen flow to patient 35 via patient-machine interface 30. The auto flow condition signal from ratio detector 60 is also provided via lines 97 and 97' to one of the terminals of double-pole, double-throw (DPDT) selector switch 105. Line 99 delivers the auto flow condition signal to the ON input of memory for operating mode 85. The other terminal of DPDT switch 105 is connected to driving power for alarms 110. When DPDT switch 105 is placed in the on position, line 97' is connected to lines 52 (one input to memory for operating mode 85) and 99' via line 99. Alarm driving voltage 110 is connected to audible and visible alarm 75, providing driving power to alarm 75 via line 113. When DPDT switch 105 is placed in the off condition, alarm driving voltage 110 is connected to warning indicator for alarms off condition 115 via line 112. Likewise, when DPDT switch 105 is placed in the off condition, line 97' for the auto flow control signal is disconnected from line 99 and DPDT switch 105 has one terminal in an open circuit condition.

Low input voltage detector 95 is connected to regulated DC power supply 102 via line 104. The inputs to DC power supply 102 are provided on lines 101A and 101B and may be either 12 volts AC or 12 volts DC. The outputs from regulated DC power supply 102 are 5 volts and 2.5 volts. The output voltages from the regulated DC power supply 102 are used for powering the oxygen flow controlling valve 25 and integrated circuits, and as a reference voltage source. The voltage for operation of the valve 25 and the integrated circuits is delivered by line 104 to the low input voltage detector 95 for the purpose of determining the adequacy of the voltage available for operating the device. If the voltage available is found to be inadequate, low input voltage detector 95 places a signal on line 98 which, via lines 97' and 97, turns memory for alarm and low input voltage 70 ON thereby activating audible and visible alarms 75.

Finally, if driving power 87 to valve 25 is interrupted, and memory for power interruption 100 is placed in the off condition, it is necessary to reset memory 100 to again place it in the on condition and allow oxygen flow controller valve 25 to be controlled by signals from driving circuitry 65. Resetting of memory 100 may be done either by automatic power up reset 120 or manual power up reset 125. The power up reset signal is placed on line 123 and provided to the on input for memory 100.

Under normal operating conditions, the oxygen flow to the patient is stopped upon the end of inhalation and begins again upon the end of exhalation. In this manner, the preferred embodiment allows for residual carbon dioxide in patient-machine interface 30 and the oxygen tubing to be expulsed before inhalation. At a minimum, the oxygen flow prior to inhalation dilutes the carbon dioxide residual in the tubing and interface. Alternate embodiments could allow for oxygen flow to begin upon the beginning of inhalation by adjustment of the inhalation slope and level detector 50.

The preferred embodiment described herein is intended and designed to insure that the intended flow of oxygen to the patient is provided if there is a suitable supply of oxygen available. It is recognized that any device, system, or method may fail to function properly without warning or without the patient and/or attending personnel being able to anticipate a potential failure or problem. The preferred embodiment will warn the patient and/or attending personnel should the supply of oxygen not be present or should the supply of oxygen be depleted or interrupted. In addition, it is intended that the device should automatically start a continuous flow of oxygen to the patient and to be able to activate both visible and audible alarms in the event of a component failure or a failure of attending personnel to operate the device properly. The invention herein described is designed to alert or warn the patient and/or attending personnel and/or automatically start the flow of oxygen to the patient in the event of the following seven abnormal conditions:

1. Failure to connect tube, or interruption or depletion of the oxygen source.
2. Failure to connect the device to the power source, failure of the power source, temporary interruption of the power source, low operating voltage, or failure to turn on the power for the device.
3. Failure of the oxygen flow controlling valve driving circuit 65 which could prevent the flow of oxygen to a patient.
4. Failure of respiration sensor 40.
5. Inability of a patient to start the flow of oxygen with spontaneous respiration.
6. Blockage or disconnection of respiration sensor tubing 38 and/or respiration sensor 40.
7. Failure of the device to automatically start the flow of oxygen to the patient in the event of any of the above listed failure modes.

Referring to abnormal condition number one, if the device is not connected to oxygen source 10 or if the valve for oxygen source 10 is not turned on, or if oxygen source 10 should be interrupted or depleted during otherwise normal operation of the device, the red no oxygen flow indicator 27 will be energized and the audible and visible alarms 75 will also be activated. This activation will alert the patient and/or attending personnel of an abnormal operating condition. The lack of oxygen condition is detected by oxygen source sensor 20. Sensor 20 activates, as described above, closing oxygen source interruption switch 22. The control signal on line 68 causes a signal to be outputted on line 97 from ratio detector 60. The signal on line 97 is inputted into the alarm ON input of memory for alarms 70. This activates audible and visible alarms 75. If switch 105 is in the off position, and audible and visible alarms 75 are not energized, they will not sound, but warning indicator 115 will be lit up indicating an alarms off condition. The red no oxygen flow indicator 27 will continuously be lighted through line 68 by oxygen source interruption switch 22. The continuous lighting of red no oxygen flow indicator 27 will indicate to the patient and/or personnel monitoring the equipment that oxygen is not being supplied to the patient.

If there is little or no power because the patient and/or attending personnel have failed to connect the device to a power source or there is a failure of the power source, either temporary or permanent, causing inadequate voltage for normal operation of the device, oxygen will automatically be flowing continuously to the patient provided that the device has been connected to an available oxygen source 10. This is why the preferred embodiment has the oxygen flow controlling valve 25 in the normally open position. Valve 25 is normally biased in the open position so that if there is an interruption of or a drop in the operating voltage of the power source, valve 25 will automatically open and thereby provide a continuous flow of oxygen to the patient.

In the event that the operating voltage would fall low enough to prevent reliable operation of the electronic circuitry of the device, but yet be high enough to keep valve 25 closed, thereby preventing the flow of oxygen to patient 35, a low voltage detector 95 is provided to continuously monitor the output from power supply 102. If the output voltage from power supply 102 should fall below a safe operating voltage, detector 95 will deliver a signal on line 98. This signal will be provided to memory for alarm and low input voltage 70 at the alarms ON input causing audible and visible alarms 75 to activate. The signal from detector 95 will also be placed at the inhalation input to memory for operating mode 85. This causes driving circuit 65 to open valve 25 and leave valve 25 open, providing oxygen to patient 35 until the low voltage condition is corrected.

If oxygen flow controlling valve driving circuit 65 should fail in the open-circuit mode, failure condition three, valve 25 could not be energized. Therefore, the normally open valve 25 would provide a safe, continuous flow of oxygen to the patient, presenting no potential hazard. If, however, valve driving circuit 65 should fail in the short-circuit mode, valve 25 would be energized continuously, thus causing an interruption in the flow of oxygen to the patient. Power interruption switch 90 is placed in series between the driving power input on line 87, and oxygen flow controlling valve 25, and valve driving circuitry 65. During normal operation, valve driving circuitry 65 causes line 68 to cycle between a high voltage level and a low voltage level (or ground). The low voltage level occurs during the oxygen delivering cycle and the high voltage level during the time oxygen is not flowing to the patient. These signals on line 68 are delivered to the input of ratio detector 80. In the event of a malfunction or short-circuit of valve driving circuitry 65, the cycling between high and low voltage levels will be absent. The absence of a proper ratio of high to low voltage levels will trigger ratio detector 80 such that a signal will be placed upon line 81. The signal on line 81 will be inputted to the power OFF input of memory for power interruption 100. This will activate power interruption switch 90 which causes valve 25 to be de-energized, thus automatically turning on the flow of oxygen to the patient by allowing valve 25 to return to the open position.

The same signal received by detector 80 will also be received by detector 60. Since for activation, detector 80 requires a signal indicative of a ratio of valve open to valve closed outside the permissible limits necessary to activate detector 60, when detector 80 is activated detector 60 has already been activated. Detector 60 will output a signal on line 97 which will activate audible and visible alarm 75. This signal will also be provided to the inhalation input to memory for operating mode 85 via lines 97', 99, and 52. Memory 85 will deliver a signal to valve driving circuitry 65 via line 63 in an attempt to resume the normal operating cycle of the device. If this is unsuccessful, audible and visible alarm 75 will remain activated. Thus, even if valve driving circuitry 65 and power interruption switch 90 were to fail, separately or in combination, the patient and/or the attending personnel would be alerted to the problem.

If any portion of the sensor circuitry 40, for example optoelectric pair 42 (FIG. 2), should fail function properly, failure condition four, oxygen flow would be started automatically by ratio detector 60 and/or ratio detector 80. Failure of respiration sensor 40 would cause an adverse ratio of the time that the valve is open to the time that the valve is closed. A signal would be placed on line 97 at the output of ratio detector 60. Line 97 is connected to the power ON input to memory for alarms 70. A signal on line 97 would cause audible and visible alarms 75 to be activated.

If the patient cannot start the flow of oxygen with spontaneous respirations, failure condition five, oxygen flow would be started automatically by ratio detector 60 placing a signal upon line 97, thereby through 97', 99 and to the input of memory for operating mode 85. This signal would override any signals from respiration sensor 40 through the inhalation slope and level detector 50 or exhalation slope and level detector 55. This would place the oxygen flow controlling valve 25 in the open position. Simultaneously, the visible and audible alarms 75 will be activated by a signal on line 97 to the power ON input of memory 70. In this manner, the personnel attending the patient would be alerted that the patient is unable to start the flow of oxygen with spontaneous respirations.

If there should be a blockage, obstruction, or kinking of the respiration sensor tubing 38, sensor 40 could not be triggered on or off by the spontaneous respirations of the patient, failure condition six. Therefore, the device would see this failure as a failure of sensor 40 to function properly and oxygen flow to the patient would be started automatically in the manner described above.

If the automatic oxygen flow starting sub-systems of the device should fail to start the flow of oxygen to the patient for any reason, failure condition seven, the visible and audible alarms 75 will nevertheless be activated. The activation will alert the patient and/or the attending personnel that there is difficulty in the operation of the device.

Turning now to FIG. 2, a detailed schematic is shown of a first embodiment of the invention. FIG. 2 is composed of FIGS. 2A and 2B. The resistor and capacitor values in FIG. 2 are set out in Tables 1 and 2, respectively.

TABLE 1

| Resistor Values (in ohms) | | | | | |
|---|---|---|---|---|---|
| R1 | 56,000 | R17 | 47,000 | R32 | 1,000,000 |
| R2 | 6,800 | R18 | 10,000 | R33 | 100,000 |
| R3 | 2,200 | R19 | 56,000 | R34 | 470 |
| R4 | 22,000 | R20 | 56,000 | R35 | 15,000 |
| R5 | 220,000 | R21 | 56,000 | R36 | 10,000 |
| R6 | 1,000 | R22 | 470,000 | R37 | 270,000 |
| R7 | 100,000 | R23 | 27,000 | R38 | 47,000 |
| R8 | 100,000 | R24 | 68,000 | R39 | 47,000 |
| R9 | 1,000 | R25 | 68,000 | R40 | 100,000 |
| R10 | 10,000 | R26 | 47,000 | R41 | 22,000 |
| R11 | 82,000 | R27 | 470,00 | R42 | 2,200 |

TABLE 1-continued

| Resistor Values (in ohms) | | | | | |
|---|---|---|---|---|---|
| R12 | 100,000* | R28 | 2,200 | R43 | 470,000 |
| R13 | 1,000 | R29 | 18,000 | R44 | 47,000 |
| R14 | 10,000* | R30 | 18,000 | R45 | 47,000 |
| R15 | 150,000 | R31 | 100,000 | R46 | 100,000 |
| R16 | 15,000 | | | R47 | 22,000 |

*Variable

TABLE 2

| Capacitor Values (in microfarads) | | | | | |
|---|---|---|---|---|---|
| C1 | 0.00047 | C5 | 0.01 | C9 | 22 |
| C2 | 4.7 | C6 | 0.01 | C10 | 0.01 |
| C3 | 0.1 | C7 | 0.01 | C11 | 0.01 |
| C4 | 0.47 | C8 | 0.001 | C12 | 22 |

During operation, one end of the oxygen delivery tubing 13 is connected to oxygen source 10. The oxygen flows through tubing 13, pressure regulator 15 and tubing 18 to oxygen flow controlling valve 25. Oxygen flow controlling valve 25 is comprised of valve 130 and solenoid coil 135. The oxygen will flow freely into tubing 28 when oxygen flow controlling valve 130 is open. Oxygen will then flow through tubing 28 to patient-machine interface 30. Tubing 38 is extruded as a second, but distinctly separate, fluid holding tube which is extruded as an integral part of the oxygen delivery tubing. Patient-machine interface 30 is a nasal cannulae, face mask or tracheal tube. Tubing 38 connects to respiration sensor 40. Respiration sensor 40 may use mechanical, pneumatic, magnetic, electrical, resistive, conductive, or optical principles separately or in combination, to accomplish the task of identifying and signalling the inhalation and the exhalation phase of the respiratory cycle of the patient receiving oxygen therapy. In the preferred embodiment, respiration sensor 40 uses optoelectrical principles to identify and distinguish inhalation and exhalation of a patient.

Tubing 38 is connected in the machine to respiration sensor port 140. Port 140 is a cul-de-sac which is fluidly connected to flexible diaphragm 139. Light interrupting flag 148 is attached to diaphragm 139 such that light interrupting flag will allow the transmission of light between (light emitting diode)/optotransistor pair 42 when diaphragm 139 is expanded from exhalation. During inhalation, the movement of diaphragm 139 will cause flag 148 to move to block the transmission of light between LED/optotransistor pair 42. LED 42a is located to one side of flag 148 and optotransistor 42b is located to the opposite side. The LED/optotransistor pair 42 is an H21A1 slotted optical switch such as those manufactured by Motorola Corporation of Phoenix, Ariz. Light emitting diode 42a is powered by circuit 141. Circuit 141 modulates LED 42a by use of oscillation controller 145. Controller 145 is a LM556C manufactured by National Semiconductor of Santa Clara, Calif. Transistors 142 and 143 are general purpose NPN transistors such as the 2N2222, which use the output of oscillator 145 to intermittently activate LED 42a. The output signal from oscillator 145 is applied to the base of transistor 143 via line 146. When an output signal is placed on 146, saturating transistor 143, line 147 goes low and transistor 142 is open, thereby deactivating LED 42a. When the output signal from controller 145 on line 146 goes low, transistor 143 is open and line 147 is pulled high across resistor R4. The high signal on line 147 saturates transistor 142, taking line 144 low and activating LED 42a. The purpose of oscillating power circuit 141 is to save power by not having LED 42a constantly lit. Rapidly pulsing LED 42a on and off conserves power and prolongs the life of the batteries used to power this first embodiment.

During exhalation as port 140 fills with exhaled air from patient 35 via interface 30 and tubing 38, the output signal from the collector of optotransistor 42b has a negative slope. During inhalation, the slope of the output signal on line 43 is positive. Between inhalation and exhalation and between exhalation and inhalation, there is no slope to the signal on line 43. This signal is amplified as it passes through adjustable offset and gain amplifier 45. A signal on line 43 passes through operational amplifiers 150 and 155. Operational amplifiers 150 and 155 are low power operational amplifiers such as the LM324, a quad operational amplifier package containing four operational amplifiers manufactured by National Semiconductor of Santa Clara, Calif. The output of amplifier 45 is provided on path 46 to exhalation slope and level detector 55. The same signal is also provided on path 46' to inhalation slope and level detector 50. It is obvious to one skilled in the art that the signs of the slopes could be inverted to obtain the same results as described in this embodiment of the invention.

Exhalation slope and level detector 55 utilizes an operational amplifier, the output of which is operably connected to the input of a monostable multivibrator. The signal on line 46 is connected to the noninverting input of operational amplifier 175 of exhalation slope and level detector 55. The inverting input of operational amplifier 175 is connected to voltage dividing circuit 165 via line 168. Voltage dividing circuit 165 consists of two resistor pairs in parallel. Each resistor pair has two resistors in series between a reference voltage of 2.5 volts and ground. The center of each of the resistor pairs is tied to either side of one pole of a double pole, double throw (DPDT) switch 160. Pole 160a is connected to line 168 and thereby to the inverting input of operational amplifier 175. The choice of resistors R18, R19, R20, and R21 determine the two possible reference voltages at which a signal on line 168 will be applied to the inverting input of amplifier 175.

The signal from operational amplifier 175 travels on path 178 to multivibrator 180. Multivibrator 180 is a retriggerable, resettable monostable multivibrator such as the MC14528B, a dual multivibrator integrated chip manufactured by Motorola Corporation of Phoenix, Ariz. Multivibrator 180 produces a control signal on line 57 immediately after exhalation which is delivered to memory for operating mode 85 via line 57. Line 57 is connected to the oxygen flow driving circuitry OFF input of flip-flop 190. Flip-flop 190 is one-half of a dual input flip-flop 140 such as the MC14027B chip manufactured by Motorola Corporation. A driving circuitry OFF control signal on line 57 produces a signal at the inverted output of flip-flop 190. This signal passes through amplifier 192 and thence to oxygen flow controlling valve driving circuitry 65.

The signal on path 46' is connected to the inverting input of operational amplifier 176 of inhalation slope and level detector 50. The non-inverting input of operational amplifier 176 is connected to voltage dividing circuit 170 via line 169. Circuit 170 is similar to circuit 165 and the resistor pairs are accessed by throwing pole 160b of DPDT switch 160. The signal from amplifier 176 travels on path 183 to multivibrator 185. A control signal on line 52 from multivibrator 185 is provided to the driving circuitry ON input of flip-flop 190. When a control signal appears on line 52, there is no potential at the inverted output of flip-flop 190.

DPDT switch 160 allows the demand oxygen system to operate in two distinct modes. The first mode turns on the oxygen flow to patient 35 at the start of inhalation and turns the oxygen flow off to patient 35 at the start of exhalation. The second mode, which pre-flushes interface 30 of the carbon dioxide from exhalation, turns on the oxygen flow at the end of exhalation and turns the oxygen flow off at the start of exhalation. These two modes of operation are controlled by applying difference reference voltages to the inverting input of operational amplifier 175 of exhalation slope and level detector 55 and the noninverting input of operational amplifier 176 of inhalation slope and level detector 50. These alternate modes are operator selected by use of DPDT switch 160.

Memory for operating mode 85 will provide a signal to valve driving circuitry 65 to close valve 130 at the end of inhalation. In the pre-flush operating mode, at the end of exhalation, no signal is outputted from flip-flop 190 because the signal on line 57 from exhalation slope and level detector 55 is inputted to driving circuitry OFF input of flip-flop 190. When valve driving circuitry 65 is off, valve 130 is open. By opening valve 130 at the end of exhalation, the carbon dioxide concentration in patient-machine interface 30 is lessened.

When the signal on line 46 changes from a negative slope to a positive slope after inhalation, the signal will be amplified by amplifier 175. Because the signal on line 46 is provided to the noninverting input of amplifier 175, a change to positive slope will trigger multivibrator 180. Multivibrator 180 will then provide a pulse on line 57 to the driving circuitry OFF input to flip-flop 190. The signal on line 57 will cause the inverted output of flip-flop 190 to go to full potential. This signal will be provided via line 63 to driving circuitry 65, causing valve 130 to close.

Oxygen flow controlling valve driving circuitry 65 is composed of a Darlington pair of transistors 195 such as an MPSA-13 transistor. An MPSA-13 transistor is manufactured by Motorola Corporation. As is well known in the art, a Darlington pair of transistors yields a high transistor base to emitter gain. The signal from memory for operating mode 85 is provided to the base of Darlington pair 195. When a signal is placed on line 63 indicating the end of inhalation by patient 35 and an input to flip-flop 190 of driving circuitry OFF, the Darlington transistor pair 195 cause the potential on line 68 to go to ground energizing solenoid coil 135 which is operably connected to the oxygen flow controlling valve 130 thereby closing valve 130. This turns off the flow of oxygen through tubing 28 to patient 35 during the exhalation phase of patient 35's respiratory cycle. It should be noted that driving circuitry 65 may be connected so that it will supply an electrical current to activate either a normally open or a normally closed type valve 130. In addition, circuitry 65 may be connected so as to deliver a short duration pulse of electrical current to a toggle-type, normally open or normally closed valve 130.

Line 68 is connected to green oxygen flow ON indicator 67. More particularly, line 68 is connected to the noninverting input of operational amplifier 200 with pull-up resistor R31 maintaining a voltage level at the noninverting input. Operational amplifier 200 is configured for a voltage summing amplifier and the inverting input of amplifier 200 is connected to line 92 across a voltage divider formed by R29 and R30. Line 92 is connected to solenoid coil 135 and power interruption switch 90 so that a potential will be present on line 92 when power interruption switch is closed. The output of amplifier 200 is provided to the reset input of timer circuit 205. Timer 205 is a LM556C dual timer which will modulate the output voltage on line 204 when a positive signal is present on line 201 to the reset input of timer 205. A negative signal is present on line 201 from the output of amplifier 200 when driving circuitry 195 pulls the voltage on line 68 to ground and when power interruption switch 90 is closed holding line 92 at plus 5 volts. Since lines 92 and 68 are also connected to either side of solenoid coil 135, the same circumstances which cause a nagative voltage to be present on line 201, causes solenoid coil 135 to be energized, closing valve 130. Therefore, when valve 130 is closed, there will be no pulsing voltage on line 204. The voltage on line 204 will be modulated providing a pulsing signal to transistor 206 when valve 130 is open. This pulsing signal will cause intermittent energization of green LED 208 signifying that valve 130 is open. Rapidly pulsing LED 130 on and off conserves power and will prolong the life of the batteries used to power this embodiment of the invention.

Line 68 is also connected to valve open/valve closed ratio detector 80 for control of power ON/OFF. Detector 80 is comprised of an RC ratio circuit 210, the output of which is connected to the noninverting input of operational amplifier 215 acting as a DC voltage summing amplifier. The inverting input of operational amplifier 215 is connected to a voltage divider formed by resistors R38 and R39. The output of operational amplifier 215 is connected to the input of multivibrator 218. Detector 80 will detect the ratio between the time that valve 130 is open to the time that valve 130 is closed and controls the power ON and OFF through power interruption memory 100.

The signal arrives to detector 80 via line 68. The signal on line 68 passes through diode 209 such that only a positive signal on line 68 will appear at line 212. RC ratio circuit 210, comprised of resistor R37 and capacitor C9, is connected to line 212. When a signal is inputted to detectors 80 from line 68, the signal on line 212 charges capacitor C9. When no signal is inputted to detector 80 from line 68, capacitor C9 will discharge, presenting a signal on line 212. Thereby, circuit 210 will produce a signal on line 212 which is the ratio of the time that a signal is present on line 68, closing valve 130, to the time that no signal is present on line 68, opening valve 130. This signal on line 212 is connected to the noninverting input of operational amplifier 215. The output of amplifier 215 is connected to multivibrator 218. The voltage at the inverting input of amplifier 215, determined by resistors R38 and R39, will set the limit at which the ratio voltage on line 212 presents a signal on line 216 sufficient to trigger multivibrator 218 to produce an output signal on line 81.

Line 81 is connected to the off input of flip-flop 220. Flip-flop 220 is the memory for power interruption 100. When a signal on line 81 turns flip-flop 220 off, no signal will be outputted from memory for power interruption 100 on line 88 to power interruption switch 90. Power interruption switch 90 is a Darlington pair transistor 225 such a the MPSA-13 transistor. Line 88 is connected to the base of transistor 225. When no signal is present on line 88, transistor 225 will be an open circuit and the driving power input of 5 volts on line 87 will not be connected to line 92.

In order to close power interruption switch 90, power up reset 125 must provide a signal on line 123 to the power on input of flip-flop 220. This is done manually by closing single pole, single throw switch 228 for a short period of time.

Prior to the time that electrical power to the apparatus is first turned on, power interruption switch 90 is open and capacitor C12 is fully discharged. Immediately after electrical power is turned on to operate the apparatus, the ON input of flip-flop 220 is at ground potential and the output of flip-flop 220 is at ground potential, causing power interruption switch 90 to remain open. Following application of electrical power, capacitor C12 charges causing line 23 to go from ground potential to plus five volts. This rising signal is delivered by line 123 to the ON input of flip-flop 220 causing the output of flip-flop 220 to go from ground potential to plus five volts. Line 88 supplies the plus five volt signal to the base of power interruption transistor 225, closing transistor 225 and supplying power for the normal operation of valve 130.

When a potential is present on line 92 higher than the potential on line 68, current will flow through solenoid coil 135. When transistor 225 is open, the potential on line 92 will be less than the potential on line 68 and the current will flow across diode 230. Diode 230 also serves to dissipate the flyback voltage resulting from the deactivation of solenoid coil 135. When solenoid coil 135 is activated, a magnetic field is generated around coil 135 which closes valve 130. When the potential across coil 135 is turned off, the magnetic field will discharge. Before discharging, the magnetic field will induce an electrical current in deactivated coil 135. The electrical current will be in the opposite direction of the current across coil 135 which generates the magnetic field. This current and subsequent flyback voltage, is dissipated across diode 230.

Solenoid coil 135 is magnetically connected to oxygen flow controlling valve 130 in oxygen flow path 18. A primary safety feature of this embodiment of the invention is that oxygen flow controlling valve 130 is of the normally open type. In other words, oxygen will flow freely through the valve until solenoid coil 135 is energized, closing valve 130. A normally closed valve could be substituted for normally open valve 130 and would only require a reversal of the polarity of the output from oxygen flow controlling valve driving circuit 65. In addition to valve 130 being of the type which requires a continuous flow of electrical current in order to be actuated, it may be of a latching type, or alternate action type of valve, requiring only a short pulse of current to either open or close the valve.

Turning now to valve open to valve closed ratio detector for controlling alarm and automatic oxygen flow start 60, the input to detector 60 is tapped off of the output from inhalation slope and level detector 50 (line 52'). The signal on line 52' is connected to a voltage follower comprised of operational amplifier 235 via line 83'. The output of operational amplifier 235 is placed on line 237. The signal on line 237 is then processed through detector 60. Valve open to valve closed ratio detector for controlling alarm and automatic flow start 60 is constructed the same as valve open to valve closed ratio detector for control of power ON/OFF 80 discussed above. Diode 239 prevents extraneous signals from flowing in the direction from detector 60 back to the output of inhalation slope and level detector 50. A signal on 237 will pass through diode 239 to line 240. Line 240 is connected to the non-inverting input of operational amplifier 243. Line 240 is also connected to RC ratio circuit 245 comprised of capacitor C13 and resistors R43. The inverting input of amplifier 243 is connected to a voltage divider comprised of resistors R44 and R45. The output of amplifier 243 appears as a signal on line 248 which is inputted to multivibrator 250. The output of detector 60 is the output of multivibrator 250 on line 97. The difference between ratio detector 60 and ratio detector 80 is the values of the resistor and capacitor in RC ratio circuits 210 and 245. Because of the different values used, ratio detector 60 will be more sensitive than ratio detector 80.

The input to ratio detector 60 tapped off of the output of inhalation slope and level detector 50 via line 52' is also connected via line 83 to the off input of flip-flop 255. Thus, when inhalation slope and level detector 50 indicates that patient 35 is inhaling, the output of detector 50 on line 52 turns off memory for alarm 70'. When patient 35 is having difficulty with inhalation and his efforts at inhalation are insufficient to output a signal from inhalation slope and level detector 50, no signal will be provided to ratio detector for controlling alarm 60. With no input to ratio 60, capacitor C13 will continue to discharge and the signal on line 240 will fall below that sufficient to keep the output of amplifier 243 on line 248 positive. When the signal on line 248 goes negative, multivibrator 250 outputs a signal on line 97 to the ON input of memory for alarm 70'. Memory for alarm 70' is comprised of flip-flop 255. When a signal from multivibrator 250 is outputted on line 97, flip-flop 255 turns on, providing an output signal on line 73 to no oxygen flow alarm 75'. No oxygen flow alarm 75' can be a visible alarm such as a light emitting diode or an audible alarm such as a piezo alarm, or a combination of both. No oxygen flow alarm 75' is powered by voltage on input line 110. The signal on line 73 turns on alarm 75' through the use of a transistor in a manner well known in the art with variations depending upon what type of alarms are used. The alarms will remain on until inhalation by patient 35 causes a signal to be outputted from inhalation slope and level detector 50 to lines 52' and 83 and, thus, to the OFF input of flip-flop 255.

A signal from valve open to valve closed ratio detector for controlling alarm and automatic flow start 60 will control alarm 75' in the manner described above, a signal outputted from detector 60 will also start automatic oxygen flow by providing that signal via line 97' to the ON input of flip-flop 190. This signal will provide no output from the inverted output of flip-flop 190. Thus, transistor 195 will be open, solenoid coil 135 will be deenergized, and valve 130 will remain open. Diode 260 will prevent any signal on line 97' from traveling back up line 52' to line 83 and turning off flip-flop 255. Diode 265 will prevent any signal during normal operation which is being provided to the ON input of flip-flop 190 from being provided via lines 97' and 97 to the ON input of flip-flop 255 which would erroneously set off alarm 75'.

The apparatus is controlled by regulated DC power supply 102. Power supply 102 is run off either batteries or an adaptor. Switch 270 is the main on/off power switch.

It is obvious to one skilled in the art that a low input voltage detector and/or alarm could be connected to regulated DC power supply 102 for notifying the operator and/or patient that the battery voltage has decreased to a level insufficient for reliable performance. Also, with an appropriate mechanical-to-electrical connection, an oxygen source sensor could be placed in fluid path 18 which would detect no oxygen and would cause an alarm to light up, informing the operator and/or patient that the oxygen source is depleted.

Turning now to FIG. 3, a block diagram of the preferred embodiment of the invention is described. It is well known by those skilled in the art that the logic, decision making, and controlling functions required for operation of the apparatus, which are fully described above using standard discrete components and integrated circuit logic packages, can be performed by using a microprocessor or computer directed by appropriate software. It is contemplated that the best mode of the present invention is a microprocessor-based gas flow controller. Such an embodiment will be cheaper to manufacture and smaller in size than the disclosed embodiment. The design and programming of a microprocessor-based demand oxygen system based on the embodiment hereinabove disclosed will be apparent to one of ordinary skill in the art.

FIG. 3 depicts the apparatus control by microprocessor 275. The operation of microcontroller 275 is directed by software programming. Microprocessor 275 receives input from respiration sensor 40 via signal processing circuitry 45'. Microprocessor 275 also receives input from oxygen flow controlling valve 25 in order to monitor the operation of valve 25. The fluid control apparatus consisting of oxygen source 10, oxygen pressure regulator 15, valve 25, interface 30, and respiration sensor 40 are constructed in the manner described above.

Microprocessor 275 outputs signal to visible LED alarm 75'. Alarm 75' could also be an audible alarm or a combination of audible and visible alarms. Alarm select switch 195' is a single pole, single throw switch which would indicate to microcontroller 275 whether alarms 75' are on or off. Mode select switch 160' is a single pole, single throw switch which would indicate to microprocessor 275 whether the apparatus is to operate in the inhalation oxygen flow mode or the pre-flush or exhalation to exhalation oxygen flow mode. Microprocessor 275 outputs an appropriate signal to green oxygen flow on indicator 67 such that the indicator will be lit when oxygen is flowing through valve 25. Yellow low battery indicator 95' receives a signal from microprocessor 275 detects a low input voltage. The input voltage is provided from regulated DC power supply 102 in a manner as described above. A signal on line 68 identified as the valve control signal operates valve 25. A signal on line 88' identified as emergency shut down is the power interruption signal to oxygen flow controlling valve 25 which will shut down the power to the solenoid of valve 25 when microprocessor 275 detects that the ratio of valve open to valve closed is inappropriate.

It is also obvious to one skilled in the art that a respiration rate indicator could be attached to microprocessor 275 in such a manner that signals from microprocessor 275 would be shown on a visible display which would indicate the respiration rate of patient 35.

Likewise, it is also obvious that the flow of gas being controlled by the device may be comprised of oxygen alone or a combination of oxygen and inhalation anesthetic gas. In this manner, the apparatus could be adapted for use in an anesthesia providing system.

From the foregoing description of the preferred embodiment, it will be appreciated that the present invention overcomes the drawbacks of the prior art and meets the objects of the invention cited hereinabove. In view of the teachings of the specification, it will be apparent to those skilled in the art that many modifications, substitutions, and alterations are possible in the practice of this invention. Therefore, the scope of the present invention is to be limited only by the claims below.

I claim:

1. A method for monitoring and controlling gas flow to a patient comprising the steps of:
    (a) connecting the apparatus for monitoring and controlling gas flow and a patient to gas and power sources;
    (b) connecting the patient requiring inhalation of supplemental oxygen to a patient-machine interface such as a nasal cannula or face mask with said patient-machine interface attached to a length of respiration sensor tubing and to a length of oxygen delivery tubing;
    (c) connecting said respiration sensor tubing to a respiration sensor tubing port and said oxygen delivery tubing to an oxygen output port located on the outside of the case of the apparatus with the opposite end of said respiration sensor tubing port connected to a respiration sensor and the opposite end of said oxygen output port connected to an oxygen flow controlling valve in the apparatus;
    (d) generating a signal responsive to a respiration cycle of said patient, said respiration cycle consisting of inhalation by said patient followed by exhalation by said patient, followed by a short pause period of time just prior to beginning of the next inhalation of said patient;
    (e) detecting, monitoring, and evaluating the amplitude and slope of said signal produced by said respiration sensor, said evaluation of said signal produced by said respiration sensor to be done by a control means including a microprocessor multiple times to determine if said signal from said respiration sensor was produced by inhalation by said patient or if said signal from said respiration sensor was produced by an artifact source such as ambulatory motion of said patient or by the motion of the oxygen delivery tubing or respiration sensor tubing connecting the apparatus to said patient, said control means and said microprocessor operable in a first operating mode a second operating mode;
    (f) if a first operating mode was selected, then producing a first control signal responsive to said signal at the start of inhalation in response to said slope having a first predetermined sign and said amplitude crossing a first predetermined value to start the flow of gas to said patient and producing a second control signal responsive to said signal at the end of inhalation in response to said slope having a second predetermined sign and said amplitude crossing a second predetermined value to stop the flow of gas to said patient;
    (g) if said second operating mode was selected, then producing a first control signal responsive to said signal at the end of exhalation in response to said slope having a first predetermined sign and said amplitude crossing a third predetermined value to start the flow of gas to said patient, said flow of gas starting at the end of said exhalation by said patient and continuing during the short pause period just prior to the beginning of the next inhalation by said patient to cause the flow of said gas to wash out any exhaled carbon dioxide in said patient's nasal cavity and any carbon dioxide in a nasal cannula or face mask interface used for connecting the said flow of gas from said oxygen output port to said patient, and producing a second control signal responsive to said signal at the beginning of exhalation in response to said slope having a second predetermined sign and said amplitude crossing a fourth predetermined value to stop the flow of gas to said patient during exhalation by said patient, said second predetermined sign being different than said first predetermined sign;

(h) operating a normally open valve interposed in said oxygen output port in response to said first control signal for turning gas flow in said delivery means on and in response to said second control signal for turning gas flow in said delivery means off;

(i) predetermining an acceptable ratio of inhalation time over exhalation time for a patient;

(j) determining the actual ratio of the inhalation time over exhalation time during the inhalation phase of a respiratory cycle for the patient;

(k) comparing said actual ratio to said acceptable ratio to automatically determine the adequacy or inadequacy of the oxygen flow to the patient;

(l) automatically starting the flow of oxygen to the patient if the oxygen flow has been determined to be inadequate;

(m) automatically activating visible and audible alarms if the flow of oxygen to the patient has been determined to be inadequate;

(n) automatically interrupting driving power source to said valve to force said valve open thus allowing oxygen to flow to the patient if the flow of oxygen to the patient was not started automatically after determining that the flow has been inadequate;

(o) activating visible and audible alarms if the oxygen source is inadequate or not present;

(p) automatically starting the flow of oxygen to the patient in case of low operating voltage, or interruption of the driving power, (q) detecting and using said signal having a slope opposite to the said slope of the signal produced during the inhalation phase to turn off the flow of oxygen to a patient; and (r) repeating steps (h) through (q) for a plurality of consecutive respiratory cycles.

2. The apparatus for controlling gas flow from a gas storing means to a patient as recited in claim 1, wherein said amplitude of said signal is less than a selected one of the following:

said first predetermined value if said first respiration signal was previously generated, and said second predetermined value if said second respiration signal was previously generated.

3. The apparatus for controlling gas flow from a gas storing means to a patient as recited in claim 2, wherein, after a next crossing, said amplitude of said signal is greater than the non-selected one of said first predetermined value and said second predetermined value.

4. The method of claim 1, further comprising the steps of connecting the said oxygen delivery tubing to the output port of a respiratory gas humidifier, and with a length of tubing, to connect the said oxygen delivery port of the apparatus to the input of said respiratory gas humidifier.

5. An apparatus to monitor and control the flow of gas to a patient comprising:

(a) a gas pressure regulator means for connection between a source of pressurized gas and the apparatus hereafter defined for the purpose of limiting, to a safe level, the pressure of gas delivered to a patient through the apparatus;

(b) visible and audible alarm means for alerting and/or warning the patient and/or attending personnel of abnormal operation of the apparatus;

(c) warning indicator means to indicate and to warn the patient and/or attending personnel that the alarm "on-off" selector switch is in the "alarm off" position, thereby disabling the visible and audible alarm means intended for alerting and/or warning the patient and/or attending personnel of abnormal operation of the apparatus;

(d) a gas source sensor means to detect the presence or absence of an adequate source of gas for proper operation of the apparatus and to provide a signal to activate visible and audible alarm means in the event that the gas source becomes inadequate for the safe operation of the apparatus;

(e) respiration sensing means responsive to a respiration cycle of said patient, said respiration cycle consisting of inhalation by said patient followed by exhalation by said patient, followed by a short pause period of time just prior to the beginning of the next inhalation of said patient for generating a first respiration signal during the time of inhalation by said patient and a second respiration signal during the time of exhalation by said patient;

(f) control means including a microprocessor for detecting, monitoring and evaluating the amplitude and slope of an electrical signal produced by said respiration sensing means, said evaluation of said signal produced by said respiration sensing means to be done multiple times so as to detect and determine if said signal from said respiration sensing means was produced by inhalation by said patient or if said signal from said respiration sensing means was produced by an artifact source such as ambulatory motion of said patient or by the motion of the gas delivery tubing or respiration sensing tubing connecting the apparatus to said patient, said control means and said microprocessor operable in a first operating mode and a second operating mode, said first operating mode responsive to a first respiration signal generated by said respiration sensing means at the start of inhalation for producing a first control signal in response to said slope having a first predetermined sign and said amplitude crossing a first predetermined value to start the flow of gas to said patient and responsive to a second respiration signal generated at the end of inhalation for producing a second control signal in response to said slope having a second predetermined sign and said amplitude crossing a second predetermined value to stop the flow of gas to said patient, said second selectable operating mode responsive to a first respiration signal from said respiration sensing means and generated at the end of exhalation for producing a first control signal in response to said slope having a first predetermined sign and said amplitude crossing a third predetermined value to start the flow of gas to said patient at the end of said exhalation by said patient and continuing during the short pause period of time just prior to the beginning of the next inhalation of said patient, said flow of gas starting at the end of said exhalation by said patient and continuing during the short pause period just prior to the beginning of the next inhalation by said patient to cause the flow of said gas to wash out any exhaled carbon dioxide in said patient's nasal cavity and any carbon dioxide in a nasal cannula or face mark interface used for connecting the said flow of gas from said gas flow controlling device to said patient, said second operating mode responsive to a second respiration signal generated by said respiration sensing means at the beginning of exhalation for producing a second control signal in response to said slope having a second predetermined sign and said amplitude crossing a fourth predetermined value to stop the flow of gas to said patient during exhalation of said patient, said second predetermined sign different than said first predetermined sign;

(g) a normally open valve interposed in said gas delivery means and responsive to said first control signal for turning gas flow in said delivery means on and responsive to said second control signal for turning gas flow in said delivery means off;

(h) offset and gain controlling amplification means for modification of the output signal of the inhalation and exhalation sensing means;

(i) inhalation slope and level detector means for determining the beginning of the spontaneous inhalation phase in a patient's respiratory cycle;

(j) exhalation slope and level detector means for determining the beginning of the spontaneous exhalation phase in a patient's respiratory cycle;

(k) indicator means for visible and/or audible signalling of the proper operation of the inhalation and exhalation sensing means;

(l) gas flow controlling valve means for controlling the flow of a gas;

(m) oxygen flow controlling valve driver means for controlling the operation of the gas flow controlling valve means;

(n) memory means for receiving and retaining cyclical output signals from the inhalation slope and level detector means, the exhalation slope and level detector means, and for controlling the operation of an oxygen flow controlling valve driver means;

(o) power interruption switch means for interrupting the flow of operating power to the gas flow controlling valve means in the event of a malfunction or failure of the oxygen flow controlling valve driver means;

(p) memory means for power interruption which controls the operation of the power interruption switch means to provide automatic power interruption to the oxygen flow controlling valve driver means and the gas flow controlling valve means;

(q) automatic power-up reset means to activate the "power on" section of the memory means for power interruption which controls the operation of the power interruption switch means at the time driving power is turned on to operate the apparatus;

(r) manual power-up reset means to provide for manual override by the operator of the apparatus controlled power interruption switch means;

(s) power interruption valve open over valve closed ratio detector is such that inadequate gas flow to the patient has been provided by the apparatus and to then generate and transmit a "power off" command signal to the memory for power interruption means, said memory for power interruption means then generates and transmits a "power off" control signal to the power interruption switch means for the purpose of automatically interrupting the operation of the gas flow controlling valve means and thereby starting a continuous flow of gas to be inhaled by the patient;

(t) "no" gas flow indicator means to provide indication to the patient and/or attending personnel that no gas is flowing to the patient;

(u) gas flow "on" indicator means to provide indication to the patient and/or attending personnel that gas is flowing to the patient;

(v) start of gas flow valve open over valve closed ratio detector means to detect when the valve open over valve closed ratio is such that inadequate gas flow to the patient has been provided by the apparatus and to then automatically generate and transmit a controlling signal to the "on" input of the memory for operating mode means for the purpose of causing the memory for operating mode means to generate and transmit a controlling signal to the oxygen flow controlling valve driver means to cause the flow of gas to the patient to be turned on, the controlling signal generated by the start of gas flow valve open over valve closed ratio detector means is also delivered to the "alarm on" input of the memory for alarm and low input voltage means for the purpose of causing the memory for alarm and low input voltage means to generate and deliver a control signal to activate the visible and audible alarm means of the apparatus;

(w) direct current power supply means for accepting either alternating current input source or direct current input source to supply a constant voltage, direct current output to operate the apparatus, and (x) a low voltage detector means for monitoring the output voltage of the direct current power supply means and to generate and deliver a control signal to activate the visible and audible alarm means and to simultaneously start the flow of gas to the patient in the event that the output voltage of the power supply should fall to a level below that which will guarantee proper operation of the device.

6. The apparatus of claim 5, further comprising the inclusion of:

(a) an oxygen flow controlling valve means for controlling the flow of a oxygen; said oxygen flow controlling valve means to be a normally open valve when driving and control power to the valve is absent, and (b) an oxygen flow controlling valve driver means for controlling the operation of the oxygen flow controlling valve means; said oxygen flow controlling valve driver means to supply power continuously to actuate the valve means during the exhalation phase of a patient's breathing cycle, thus causing the valve means to close.

7. The apparatus of claim 5, further comprising the inclusion of:

(a) an oxygen flow controlling valve means for controlling the flow of an oxygen; said oxygen flow controlling valve means to be a normally closed valve when driving and control power to the valve means is absent, and (b) an oxygen flow controlling valve driver means for controlling the operation of an oxygen flow controlling valve means; said oxygen flow controlling valve driver means to supply power continuously to actuate the valve during the inhalation phase of a patient's breathing cycle, thus causing the valve means to open.

8. The apparatus of claim 5, further comprising the inclusion of:

(a) an oxygen flow controlling valve means for controlling the flow of oxygen; said oxygen flow controlling valve means to be a normally open valve when driving and control power to the valve is absent at the time the device is first turned on, said oxygen flow controlling valve mean requiring only a momentary pulse of electrical current to close said valve means, and a second momentary pulse of electrical current to open the valve means, and (b) an oxygen flow controlling valve driver means for controlling the operation of an oxygen flow controlling valve means; said oxygen flow controlling valve driver means to supply only a momentary pulse of electrical current to close said valve during the exhalation phase of a patient's breathing cycle, and a second momentary pulse of electrical current to open the valve means during the inhalation phase of a patient's breathing cycle.

9. The apparatus of claim 5, further comprising the inclusion of:

(a) an oxygen flow controlling valve means for controlling the flow of oxygen; said oxygen flow controlling valve means to be a normally closed valve when driving and control power to the valve is absent at the time the device is first turned on, said oxygen flow controlling valve means requiring only a momentary pulse of electrical current to open said valve, and a second momentary pulse of electrical current to close the valve, and (b) an oxygen flow controlling valve driver means for controlling the operation of an oxygen flow controlling valve means; said oxygen flow controlling valve means to supply only a momentary pulse of electrical current to open the oxygen flow controlling valve means during the inhalation phase of a patient's breathing cycle, and a second momentary pulse of electrical current to close the valve means during the exhalation phase of a patient's breathing cycle.

* * * * *